United States Patent
Hochenberger et al.

(10) Patent No.: US 6,363,779 B1
(45) Date of Patent: *Apr. 2, 2002

(54) PRESSURE SENSOR FOR AN INTERNAL COMBUSTION ENGINE HAVING AN INTAKE TUBE

(75) Inventors: Hans-Martin Hochenberger, Schwieberdingen; Winfried Kuhnt, Stuttgart, both of (DE)

(73) Assignee: Robert Bosch GmbH, Stuttgart (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/644,024

(22) Filed: May 9, 1996

(30) Foreign Application Priority Data

May 13, 1995 (DE) .......................... 195 17 676

(51) Int. Cl.⁷ ............................. G01M 15/00
(52) U.S. Cl. ................................ 73/118.2
(58) Field of Search ................. 73/118.2, 861.47, 73/861.65, 861.66

(56) References Cited

U.S. PATENT DOCUMENTS

| | | | | |
|---|---|---|---|---|
| 4,320,665 A | * | 3/1982 | Cain ....................... | 73/861.65 |
| 4,561,302 A | * | 12/1985 | Sumal et al. ............. | 73/118.2 |
| 4,624,146 A | * | 11/1986 | Nakagawa ............... | 73/861.66 |
| 4,677,858 A | * | 7/1987 | Ohnhaus ................... | 73/861.65 |
| 4,717,159 A | * | 1/1988 | Alston et al. ............ | 73/861.65 |
| 4,972,702 A | * | 11/1990 | Sakaue ...................... | 73/118.2 |
| 5,186,044 A | * | 2/1993 | Igarashi et al. ........... | 73/118.2 |
| 5,325,712 A | * | 7/1994 | Tsutsui et al. ............. | 73/118.2 |
| 5,365,795 A | * | 11/1994 | Brower, Jr. ............... | 73/861.65 |
| 5,383,356 A | * | 1/1995 | Zurek et al. ............... | 73/118.2 |
| 5,415,029 A | * | 5/1995 | Uchiyama et al. ......... | 73/118.2 |
| 5,419,187 A | * | 5/1995 | Uchiyama .................. | 73/118.2 |
| 5,467,648 A | * | 11/1995 | Igarashi et al. ............ | 73/118.2 |
| 5,537,870 A | * | 7/1996 | Zurek et al. ............... | 73/118.2 |
| 5,546,794 A | * | 8/1996 | Kuhn et al. ................ | 73/118.2 |
| 5,555,870 A | * | 9/1996 | Asano ....................... | 73/118.2 |
| 5,563,340 A | * | 10/1996 | Clowater et al. .......... | 73/118.2 |

FOREIGN PATENT DOCUMENTS

| | | |
|---|---|---|
| DE | 4317312 | 12/1994 |
| JP | 60 093328 | 5/1985 |
| JP | 61 246642 | 11/1986 |

* cited by examiner

*Primary Examiner*—Eric S. McCall
(74) *Attorney, Agent, or Firm*—Ronald E. Greigg

(57) ABSTRACT

A pressure sensor that is mounted on an intake tube of an internal combustion engine which prevents icing of the pressure connection. The pressure sensor of the invention has a stublike pressure connection, which extends from an inner wall of an intake tube to approximately the middle of the intake tube or beyond the middle, and as a result the risk of icing of the pressure sensor is considerably reduced. A pressure sensor is intended especially for mixture-compressing internal combustion engines with externally supplied ignition.

7 Claims, 1 Drawing Sheet

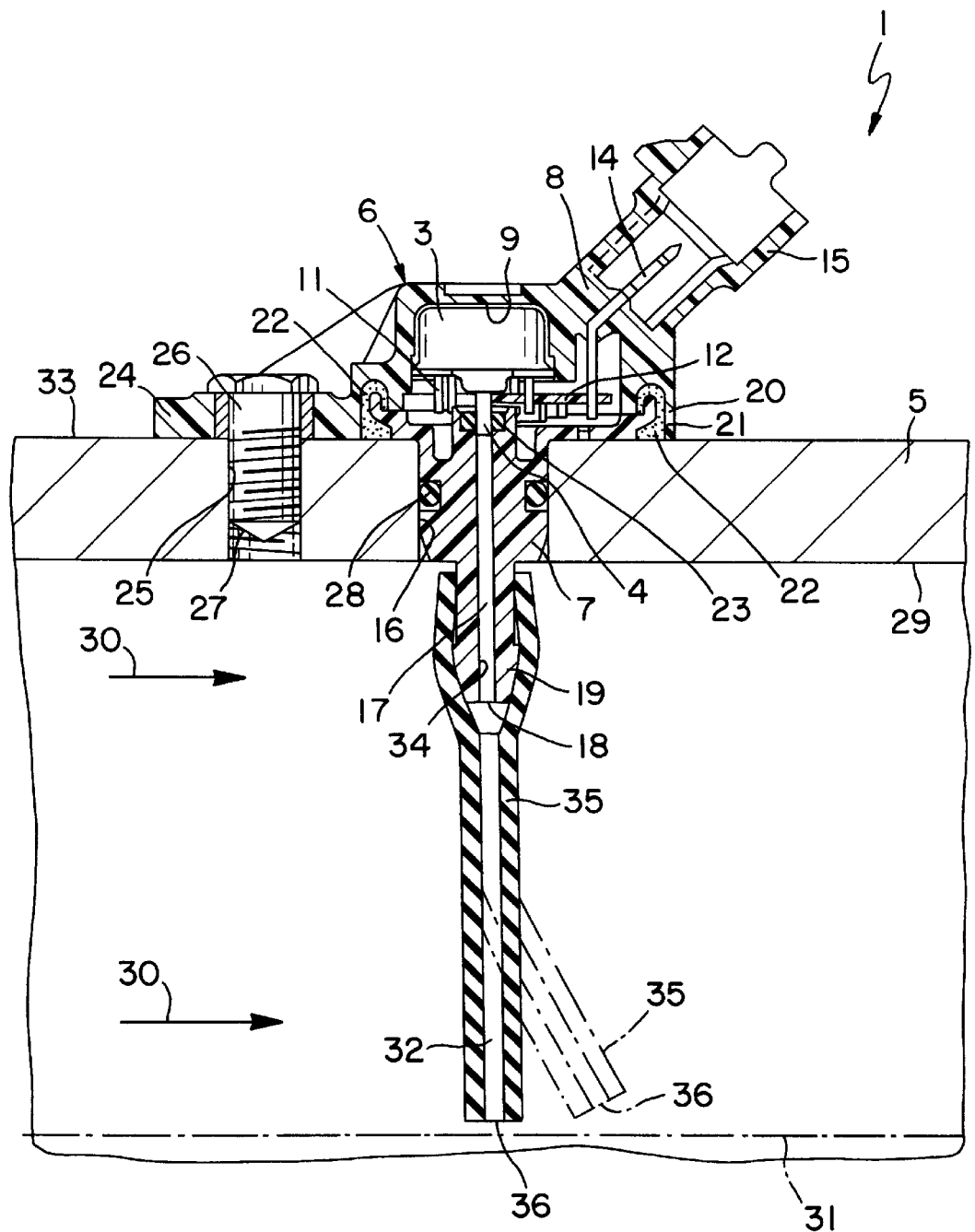

PRESSURE SENSOR FOR AN INTERNAL COMBUSTION ENGINE HAVING AN INTAKE TUBE

BACKGROUND OF THE INVENTION

The invention is based on a pressure sensor for an internal combustion engine having an intake tube. A known pressure sensor (German Offenlegungsschrift 43 17 312) has a plastic housing with a stublike pressure connection, and in the state in which it has been installed on the intake tube it is essentially flush with an inner wall of the engine intake tube, or protrudes from it by only a few millimeters. In such pressure sensors mounted directly on the intake tube, however, there is the risk of icing up of the pressure connection, so that in the worst case, failure of the pressure sensor can occur. The risk of icing is especially high in engines with exhaust gas recirculation and crankcase venting into the intake tube, since the flowing medium has a high proportion of water dissolved in gaseous form, which at low temperature can precipitate out in the form of ice, predominantly in the interior of a thin metal sensor tubule of a pressure measuring instrument of the pressure sensor.

OBJECT AND SUMMARY OF THE INVENTION

The pressure sensor of the invention has the advantage over the prior art that icing up of the pressure sensor is precluded with very great certainty. Advantageously, the deposit of liquid components of the medium flowing within the intake tube on the pressure sensor is also prevented, thus further reducing the danger of icing of the pressure sensor.

By means of the provisions recited herein, advantageous further features of and improvements to the pressure sensor are possible. It is especially advantageous that existing pressure sensors can be retrofitted in a simple way without having to make major structural changes, so that the production costs rise only slightly. Moreover, the pressure sensor of the invention advantageously requires no additional space at the installation site of the pressure sensor.

The invention will be better understood and further objects and advantages thereof will become more apparent from the ensuing detailed description of a preferred embodiment taken in conjunction with the drawings.

BRIEF DESCRIPTION OF THE DRAWINGS

The sole FIGURE of the drawing shows an exemplary embodiment of the invention in simplified form.

DETAILED DESCRIPTION OF THE PREFERRED EMBODIMENT

In the drawing, a pressure sensor 1 is shown whose essential component is a pressure measuring instrument, embodied for instance in the form of a sensor cell 3, which is accommodated in a housing 6 of the pressure sensor 1. The housing 6 is in two parts and is composed of a stublike pressure connection 7 and a caplike housing part 8. The pressure connection 7 and the housing part 8 are preferably made of plastic, for instance by plastic injection molding. The sensor cell 3 is made of metal and is accommodated in a tublike indentation 9 in the housing part 8 into which it is inserted with positive engagement. The sensor cell 3 is held in the tublike indentation 9 by an adhesive, for instance, so that except for the entrance of a thin metal sensor tubule 4 mounted on the sensor cell 3, the sensor cell 3 is hermetically sealed off from its surroundings. The known purpose of the pressure sensor 1 is to measure the internal pressure of a medium flowing in an intake tube 5 of the engine, in particular the air aspirated by the engine. By means of the internal pressure of the intake tube and the engine rpm, it is possible to determine the quantity of air aspirated by the engine. The flow direction of the medium in the intake tube 5 is indicated in the drawing by arrows 30 and extends from left to right.

The sensor cell 3 comprises a sensor chip made of silicon, into which a pressure membrane is etched. A change in pressure causes expansion of the pressure membrane, which is detected via changes in resistance (this is known as the piezoresistive effect). The evaluation circuit, including calibration, is integrated into the sensor chip. The pressure to be measured is carried via the sensor tubule 4 and a glass base provided in the interior of the sensor cell to a back side of the pressure membrane, which communicates with a reference vacuum, so as to enable measuring the absolute pressure. The output signal of the evaluation circuit is carried to a plug contour 15 embodied on the housing part 8 via electrical conductors 11 which are connected with a printed circuit board 12 and a bent metal pin 14 mounted on the printed circuit board 12. The plug contour 15 serves to receive an insertable plug, so that via the plug the electrical signals of the pressure measuring instrument, that is, of the evaluation circuit, of the sensor chip can be carried to an electronic control unit.

The sensor tubule 4 of the censor cell 3 discharges into a through opening 17, provided in the pressure connection 7, that extends from the sensor tubule 4 to an end 18 of the pressure connection 7 that is open toward the flowing medium, so that there is communication from the interior of the sensor cell 3 to the flowing medium via the sensor tubule 4 and the pressure connection 7. A sealing ring 23, embodied for instance as an O-ring, seals off the sensor tubule 4 in the pressure connection 7. The pressure connection 7 is mounted on side walls 20 of the housing part 8 and is retained, for instance in grooves 21, with the aid of an adhesive 22 placed there. The side of the housing part 8 has a formed-on feature 24 with an opening 25 into which a screw 26 can be inserted, so that the pressure sensor 1 can for instance be secured firmly by a bolt threaded into the female thread 27 on the intake tube 5. On installation, the pressure sensor 1 is introduced by its stublike pressure connection 7 into a through opening 16 of the intake tube 5, whereupon with a connection part 19 it protrudes from an inner wall 29 of the intake tube 5 into the intake tube. A seal 28, for instance in the form of an O-ring, provided between the inner wall 29 and an outer wall 33 of the intake tube 5 on the pressure connection 7, seals off the atmosphere from the flowing medium.

According to the invention, the stublike pressure connection 7 of the pressure sensor 1 extends relatively far from the inner wall 29 of the intake tube 5 into the flowing medium, so that the open end 18 of the pressure connection 7 extends approximately as far as a middle of the intake tube 5, identified by a longitudinal axis 31, or even beyond the middle of the intake tube 5. The pressure connection 7, which is embodied with a relatively long length, prevents the possibility of icing of the pressure connection 7 at low temperature, especially on an inside surface 34 of the through opening 17 of the pressure connection 7 and on the sensor tubule 4, so that a free through opening 17, or communication from the intake tube 5 to the sensor cell 3, is always available.

As shown in the drawing, the pressure connection 7 may also have a shorter length, however. For instance, it is essentially possible to use commercially available pressure sensors with a shorter pressure connection 7, and to lengthen the pressure connection by means of a hose 35, which can be slipped over the pressure connection 7 of the connection part 19, for instance, and at least partly surrounds the pressure connection 7, in such a way that the through opening 17, via an inner opening 32 of the hose 35, extends with an open end 36 of the hose likewise approximately as far as the middle of the intake tube 5 or even beyond the middle of the intake tube 5. The cross section of the internal opening 32 of the hose 35 changes, for instance at the end 18 of the pressure connection 7, via a conically converging part, into a somewhat larger opening cross section than the through opening 17, for instance. The cross section of the internal opening 32 of the hose 35 is chosen to be small enough that the internal opening 32 cannot become stopped up or plugged by dirt and contaminants, yet there is adequate hindrance to diffusion.

The hose 35 comprises fuel-resistant plastic and is made from fluorocaoutchouc, for instance. The hose 35 is embodied flexibly and, as shown in the drawing, can be bent more or less in the flow direction 30 of the medium by the flowing medium. The flexing motion of the hose 35 occurring during engine operation also makes it possible for any freezable liquid ingredients of the medium that might have collected in the hose 35 to be shaken off and carried away by the medium, thus still further reducing the risk of icing of the pressure sensor 1. The flexibly embodied hose 35 also has the effect that resonance occurring in the intake tube 5 can reach as far as the pressure measuring instrument of the sensor cell 3 only in extremely attenuated form, and as a result a precise pressure measurement is made.

The foregoing relates to a preferred exemplary embodiment of the invention, it being understood that other variants and embodiments thereof are possible within the spirit and scope of the invention, the latter being defined by the appended claims.

What is claimed and desired to be secured by Letters Patent of the United States:

1. A pressure sensor for an internal combustion engine comprising an intake tube, said intake tube including a central passage through which a medium flows, said pressure sensor including a housing, said housing is secured to an outer wall surface of said intake tube and houses a pressure measuring instrument, a single elongate pressure line that is connected to and extends from said pressure measuring instrument into said intake tube in communication with and transverse to the medium flowing in the intake tube, said elongate pressure line includes a single through opening that extends from the pressure measuring instrument to an open end of said pressure line, said pressure line is embodied as a flexible hose which has a length sufficient to extend into said intake tube, such that said open end is situated at least at a longitudinal axis of the intake tube (5) whereby an elongate length of said flexible hose has sufficient length to prevent icing of the pressure line.

2. A pressure sensor of claim 1, in which the flexible hose (35) is slipped over an end of a sensor tubule.

3. A pressure sensor of claim 1, in which the hose (35) comprises plastic.

4. A pressure sensor of claim 1, in which the flexible pressure line of the pressure sensor (1) extends with the end opening to a position at least in a vicinity of said longitudinal axis.

5. A pressure sensor of claim 1, in which said pressure line of the pressure sensor (1) extends with the end opening at a position at least beyond the longitudinal axis.

6. A pressure sensor of claim 1, in which said hose comprises fluorocaoutchouc.

7. A pressure sensor for an internal combustion engine comprising an intake tube through which a medium flows, a housing including first and second housing parts, said first housing part is secured to an outer wall surface of said intake tube, a through opening (16) extends through a wall of said intake tube, said second housing part forms a pressure connection, said pressure connection includes a first portion that extends through said through opening (16) in said intake tube and a second portion that extends into said intake tube transverse to the flowing medium, pressure sensor cell (3) secured within said first housing part, a printed circuit board (12) electrically connected with said pressure sensor cell and to an electrical plug, a through opening (17) in said first portion of said second housing part which connects with a sensor tubule of said sensor cell, said second portion of said housing part including a portion of said through-opening (17) and extends into said intake tube in communication with and transverse to a flowing medium in said intake tube, said through opening having an open end, said open end of said through opening is located approximately at a longitudinal axis of said intake tube whereby said through opening has sufficient length to prevent icing in the through opening.

* * * * *